(12) United States Patent
Ely et al.

(10) Patent No.: US 8,133,284 B2
(45) Date of Patent: *Mar. 13, 2012

(54) HIP PROSTHESIS WITH MONOBLOCK CERAMIC ACETABULAR CUP

(75) Inventors: K. Scott Ely, Austin, TX (US); Ashok C. Khandkar, Salt Lake City, UT (US); Ramaswamy Lakshminarayanan, Salt Lake City, UT (US); Aaron A. Hofmann, Salt Lake City, UT (US)

(73) Assignee: Amedica Corporation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/661,991

(22) Filed: Mar. 26, 2010

(65) Prior Publication Data

US 2010/0228354 A1 Sep. 9, 2010

Related U.S. Application Data

(60) Continuation of application No. 11/203,047, filed on Aug. 12, 2005, now Pat. No. 7,695,521, which is a continuation-in-part of application No. 10/987,415, filed on Nov. 12, 2004, now Pat. No. 7,666,229, which is a division of application No. 10/171,376, filed on Jun. 13, 2002, now Pat. No. 6,881,229, said application No. 11/203,047 is a continuation-in-part of application No. 11/040,477, filed on Jan. 20, 2005, now abandoned.

(60) Provisional application No. 60/298,669, filed on Jun. 14, 2001, provisional application No. 60/287,824, filed on May 1, 2001.

(51) Int. Cl.
*A61F 2/32* (2006.01)

(52) U.S. Cl. .................. 623/22.11; 623/22.38; 623/22.3; 623/22.21; 623/22.15; 623/22.16

(58) Field of Classification Search ............... 623/22.11, 623/22.17, 22.21, 22.24, 22.28, 22.32, 22.38
See application file for complete search history.

(56) References Cited

U.S. PATENT DOCUMENTS

| | | | | |
|---|---|---|---|---|
| 4,327,449 A * | 5/1982 | Charnley | ................ | 623/22.39 |
| 5,098,449 A * | 3/1992 | Hwang et al. | ................ | 51/307 |
| 5,395,401 A * | 3/1995 | Bahler | ................ | 623/20.29 |
| 5,871,547 A * | 2/1999 | Abouaf et al. | ................ | 623/22.15 |
| 6,080,195 A * | 6/2000 | Colleran et al. | ................ | 623/20.32 |
| 6,090,144 A * | 7/2000 | Letot et al. | ................ | 623/20.34 |
| 7,695,521 B2 * | 4/2010 | Ely et al. | ................ | 623/22.21 |
| 7,780,738 B2 * | 8/2010 | Khandkar et al. | ................ | 623/22.15 |
| 2002/0058997 A1 * | 5/2002 | O'Connor et al. | ................ | 623/20.32 |
| 2002/0062154 A1 * | 5/2002 | Ayers | ................ | 623/23.76 |

* cited by examiner

*Primary Examiner* — David Isabella
*Assistant Examiner* — Jonathan R Stroud
(74) *Attorney, Agent, or Firm* — Mintz, Levin, Cohn, Ferris, Glovsky & Popeo PC

(57) ABSTRACT

An improved hip prosthesis includes an acetabular cup bearing component constructed from a relatively hard and high strength ceramic material for articulation with a ball-shaped femoral head component which may be constructed from a compatible ceramic or metal material. In one form, the acetabular cup further includes a ceramic porous bone ingrowth surface adhered thereto for secure ingrowth attachment to natural patient bone.

13 Claims, 3 Drawing Sheets

HIP PROSTHESIS WITH MONOBLOCK CERAMIC ACETABULAR CUP

The present application is a continuation of U.S. patent application Ser. No. 11/203,047, filed Aug. 12, 2005, now U.S. Pat. No. 7,695,521 which is hereby incorporated by reference in its entirety, which is a continuation-in-part of U.S. application Ser. No. 10/987,415 (now U.S. Pat. No. 7,666,229), filed Nov. 12, 2004, which is a division of U.S. Ser. No. 10/171,376 (now U.S. Pat. No. 6,881,229), filed Jun. 13, 2002, which in turn claims the benefit of U.S. Provisional Application No. 60/298,669, filed Jun. 14, 2001.

U.S. patent application Ser. No. 11/203,047 is also a continuation-in-part of U.S. Ser. No. 11/040,477, filed Jan. 20, 2005, now abandoned, which in turn claims the benefit of U.S. Provisional Application No. 60/287,824, filed May 1, 2001.

BACKGROUND OF THE INVENTION

This invention relates generally to improvements in hip joint prostheses, particularly with respect to an improved acetabular cup bearing component constructed from a relatively hard and relatively high strength ceramic material. The ceramic acetabular cup is designed for direct articulation against an associated femoral head component formed from a compatible ceramic or metal material, with minimal component wear to achieve substantially optimal prosthesis service life. The present invention thus permits elimination of a conventional polymer-based bearing insert thereby also eliminating undesirable wear debris associated therewith.

Hip prostheses generally comprise a femoral component adapted for fixation to an upper end of the patient's femur, and defining a generally ball-shaped head for articulation relative to an acetabular cup component which is adapted in turn for seated fixation within the patient's acetabulum. A polymer-based bearing insert such as a cup-shaped component formed from a typically high density or high molecular weight polyethylene (PE) or the like is normally fitted between the femoral head and the acetabular cup to accommodate smooth and relatively low-wear articulation between these components.

However, clinical studies have shown that significant wear debris can be generated and released by the polymeric bearing insert over a period of time, and further that a principle contributing factor to implant failure is osteolysis attributable at least in part to the presence of such polymer-based wear debris. More particularly, such studies have shown that PE wear debris released into peri-implant tissues appears to elicit a deleterious biological reaction, incorporating foreign body giant cell and macrophage cell responses leading to undesirable bone resorption, with eventual loosening and failure of the prosthetic implant. As a result, alternative prosthesis constructions have proposed improvements in and to the polymer-based bearing insert, such as the use of heavily cross-linked polyethylene materials. Other alternative prostheses have been proposed using rigid-on-rigid components, such as ceramic-on-ceramic or metal-on-metal, thereby eliminating the polymer-based bearing insert and wear debris associated therewith.

In general, ceramic hip prosthesis components have shown promise for use in a ceramic-on-ceramic or alternately in a ceramic-on-metal articulating interface, thereby completely eliminating the polymer-based bearing insert. Such prosthesis constructions, when formed with a good surface finish and conformal surface geometry, have demonstrated a relatively low coefficient of friction and resultant substantial reduction in component wear in comparison with ceramic-polymer or metal-polymer articulatory interfaces. However, the major limitation on the use of ceramic components particularly such as alumina-based ceramic materials has been an unacceptably high rate of brittle fracture occurring within a post-surgical follow-up period ranging from a few months to several years. In this regard, ceramic materials generally exhibit relatively low toughness and are thus prone to brittle fracture.

U.S. Publication US 2003/0153984 discloses an improved ceramic material for use in joint prostheses, such as hip prostheses, wherein a ceramic-on-ceramic or a ceramic-on-metal articulatory interface is defined. The improved ceramic material comprises a doped silicon nitride ($S_3N_4$) having relatively high hardness, tensile strength, elastic modulus, lubricity, and fracture toughness. Specifically, the improved doped silicon nitride ceramic has a flexural strength greater than about 700 Mega-Pascal (MPa) and a fracture toughness greater than about 7 Mega-Pascal root meter ($MPam^{0.5}$). This high strength and high toughness doped silicon nitride ceramic achieves ultra-low wear over an extended service life, with dramatically reduced risk of brittle fracture.

In addition, U.S. Pat. No. 6,846,327 discloses improved ceramic materials for bone graft applications, wherein the ceramic material is designed to mimic structural characteristics of natural patient bone by including first and second regions of comparatively lower and higher porosity to respectively mimic natural cortical and cancellous bone structures. The preferred ceramic materials disclosed exhibit a flexural strength greater than about 500 Mega-Pascal (MPa) and a fracture toughness greater than about 5 Mega-Pascal root meter ($MPam^{0.5}$). In use, the relatively low porosity region of the ceramic material provides high structural strength and integrity, whereas the higher porosity region is suitable for bone ingrowth to achieve secure and stable implant affixation.

The present invention comprises an improved hip joint prosthesis particularly wherein the acetabular cup component thereof is constructed from an improved high strength and high toughness ceramic material as disclosed, e.g., in U.S. Publi. US 2003/0153984 and/or U.S. Pat. No. 6,846,327.

SUMMARY OF THE INVENTION

In accordance with the invention, an improved hip prosthesis includes an acetabular cup bearing component constructed from a relatively high strength and high toughness ceramic material for ultra-low wear articulation with a ball-shaped femoral head component which may be constructed from a compatible ceramic or metal material. In one form, the acetabular cup further includes a ceramic porous bone ingrowth surface for secure ingrowth affixation to natural patient bone.

In one preferred form of the invention, a unipolar hip joint prosthesis includes the ceramic acetabular cup having a generally shell-shaped or cup-shaped geometry defining a relatively low porosity substrate in combination with a comparatively higher porosity bone ingrowth surface. The low porosity ceramic substrate defines a downwardly open, part-spherical cavity for receiving and articulating with a ball-shaped femoral head of a femoral component, wherein the femoral head may be constructed from a compatible and preferably identical high strength and high toughness ceramic material, or alternately from a compatible metal material such as biocompatible cobalt chrome alloy or the like. The higher porosity ceramic bone ingrowth surface extends over an upper surface of the acetabular cup for suitable seated contact within a prepared patient acetabulum, for secure affixation thereto by bone ingrowth.

The ceramic acetabular cup of the hip prosthesis may incorporate a lower free circumferential edge or margin defined by a pair of shallow relief segments formed at diametrically opposed positions corresponding with the flexion/extension plane. The inclusion of these relief segments beneficially provides the patient with an enhanced range-of-motion (ROM).

The relief segments may be in the form of cutouts or recesses. Alternatively, the acetabular cup may employ a single cutout or relief, or multiple cutouts or reliefs may be used. Further the cutouts or reliefs can be symmetrically configured or asymmetrically configured. For example, the cutouts or reliefs can be diametrically oppositely disposed, spaced adjacent to each other, or spaced in other circumferential orientations.

Other features and advantages of the present invention will become apparent from. the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 2:
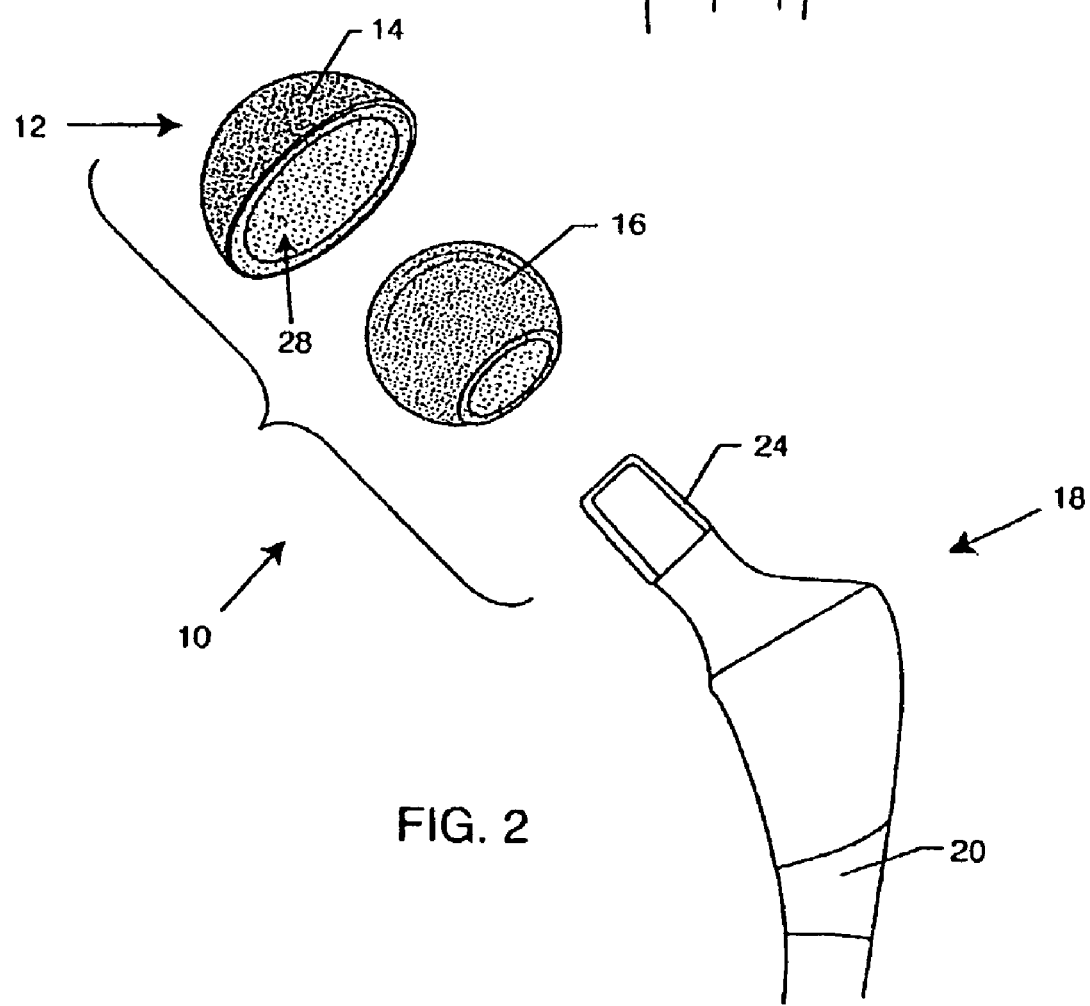
FIG. 2 is an enlarged and exploded perspective view showing components of an improved hip prosthesis embodying the novel features of the invention.
Figure 3:
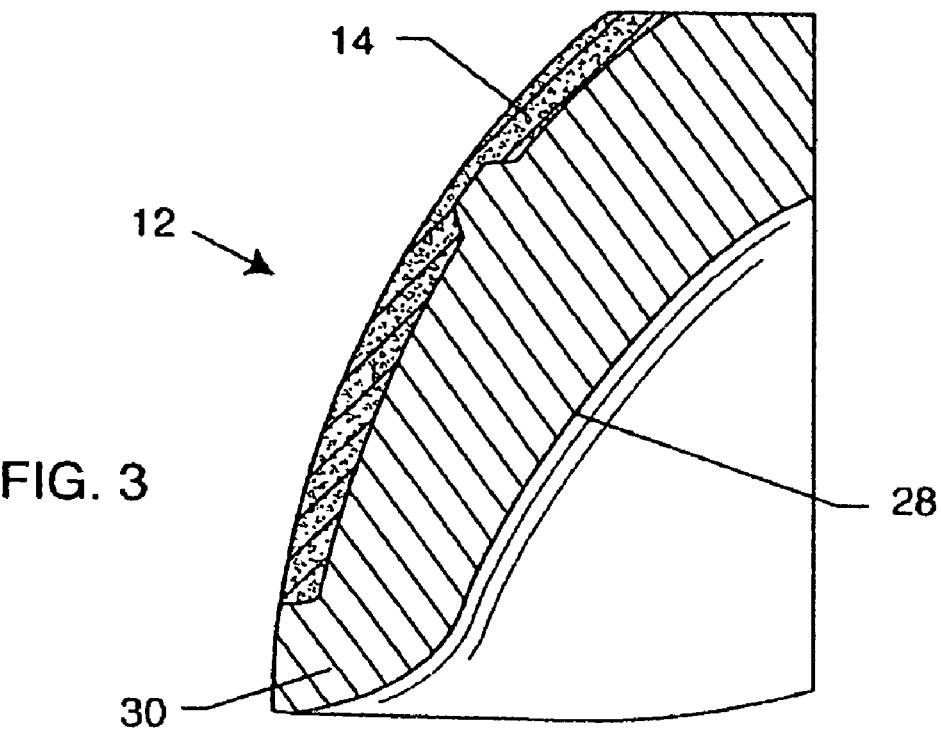
FIG. 3 is a further enlarged and fragmented sectional view depicting details of an acetabular cup used in the hip prosthesis of FIG. 2.
Figure 4:
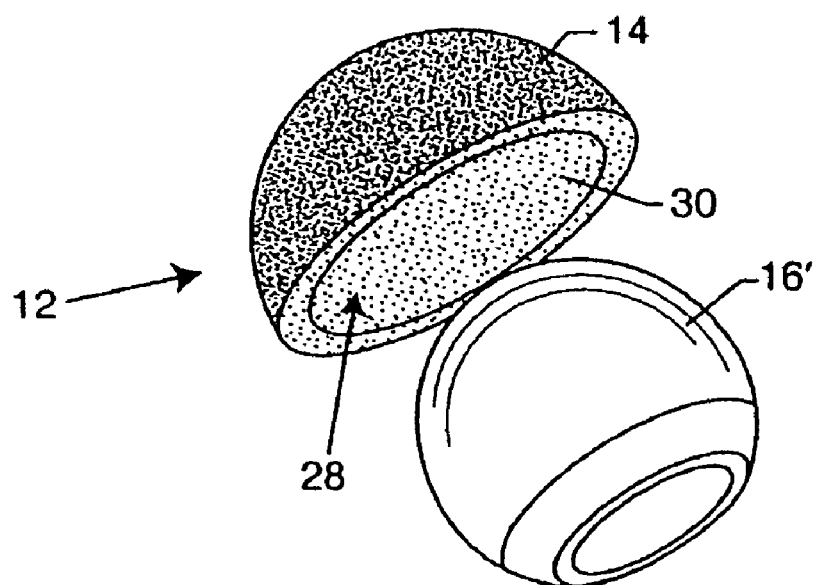
FIG. 4 is an exploded perspective view showing one alternative preferred form of a hip prosthesis.

As shown in the exemplary drawings, an improved hip prosthesis referred to generally in one preferred form by the reference numeral 10 in FIGS. 2-3 includes an acetabular cup 12 constructed from a relatively hard and high strength ceramic material which may also incorporate a relatively porous ceramic bone ingrowth surface 14 for secure affixation to patient bone. The cup 12 is designed for articulation with other prosthesis components such as a ball-shaped femoral head component 16 which may be constructed from a hard and high strength material such as a compatible and preferably identical ceramic material, or a biocompatible metal material (FIG. 4). The resultant ceramic-on-ceramic or ceramic-on-metal articulatory interface beneficially exhibits ultra-low wear over an extended service life, while additionally permitting elimination of traditional polymer-based bearing inserts and wear debris problems associated therewith.

Figure 1:
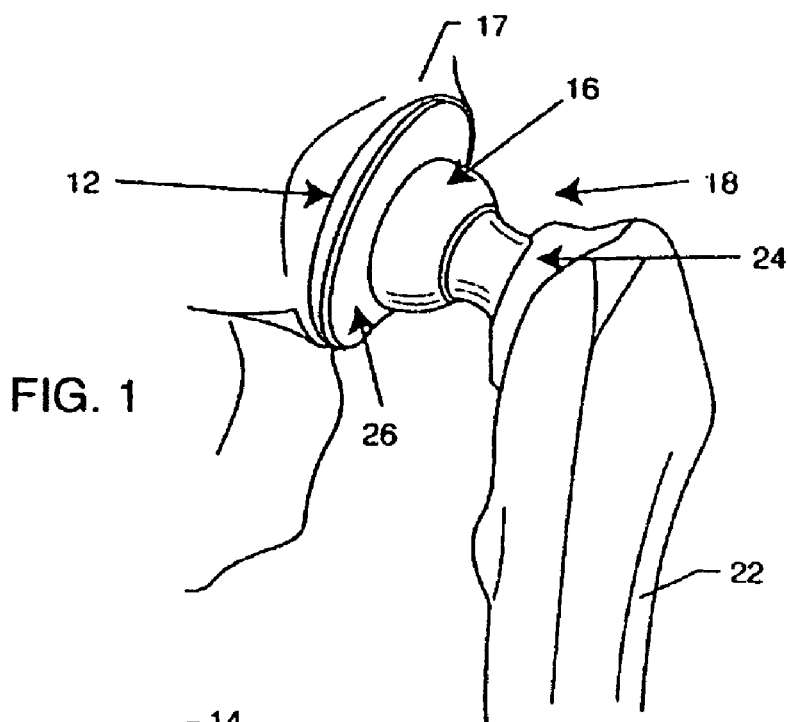
FIG. 1 is a fragmented perspective view illustrating an exemplary hip prosthesis in an installed position affixed to a patient's femur and acetabulum.

FIG. 1 illustrates a traditional hip prosthesis construction for repairing or replacing the natural anatomical ball-and-socket human hip joint. More specifically, FIG. 1 shows an acetabular cup 12 seated and/or affixed within the patient's natural acetabulum or socket 17, in combination with a femoral component 18 including an elongated stem 20 (FIG. 2) seated within a resected upper end of the patient's femur bone 22, an upwardly protruding femoral neck 24, and the ball-shaped femoral head 16 mounted or otherwise formed on an upper end of the neck 24. Accordingly, a generally cup-shaped bearing insert 26 formed typically from a polymer-based material such as a high density or high molecular weight polyethylene (PE) or the like is normally fitted between the acetabular cup 12 and the femoral head 16 to accommodate smooth articulation between these components. However, as previously noted herein, premature prosthesis failure has been attributed to the generation and accumulation of polymer-based wear debris associated with the bearing insert 26. A further drawback to the use of polymer-based inserts is the higher thickness of the construct, restricting its application to larger bone patients capable of receiving the larger sizes, and thus preventing the use of larger diameter heads in smaller bone patients.

Accordingly, the present invention is particularly directed to the provision of an improved hip joint prosthesis 10 constructed in any one of a plurality of alternative preferred forms, to include improved implantable and biocompatible materials designed for achieving ultra-low wear as a consequence of component articulation over an extended service life or duty cycle, using a ceramic-on-ceramic or a ceramic-on-metal articulatory interface, and omitting use of the traditional polymer-based bearing insert.

The present invention is also particularly directed to the provision of an improved hip joint prosthesis 10 constructed in any one of a plurality of alternative preferred forms, to include improved implantable and biocompatible materials designed for achieving a thinner overall acetabular cup diameter, and as a consequence, providing the ability to use larger diameter heads on smaller bone patients than otherwise possible, using a ceramic-on-ceramic or a ceramic-on-metal articulatory interface, and omitting the use of traditional polymer-based bearing inserts.

FIGS. 2-3 illustrate the improved hip prosthesis 10 in one preferred unipolar form. As shown, the acetabular cup 12 has a generally cup-shaped or shell-shaped geometry defining a downwardly open part-spherical and substantially hemispherical cavity 28. This shell-shaped acetabular cup 12 has a size selected for substantially conformal seated reception into the generally matingly shaped acetabulum or socket 17 (FIG. 1) which may be surgically prepared as by removal of accumulated calcium deposits or other procedures known in the art. Importantly, in accordance with a primary aspect of the invention, the acetabular cup 12 is formed from a relatively high strength and high toughness or high hardness ceramic material defining a part-spherical substrate 30 lining the cavity 28 to define an articulation surface for receiving and articulating against the ball-shaped femoral head 16.

More specifically, the preferred ceramic material used for constructing the ceramic acetabular cup 12 of the present invention comprises a high flexural strength and high fracture toughness ceramic material particularly such as a doped silicon nitride ($Si_3N_4$) having relatively high hardness, tensile strength, elastic modulus, lubricity, and fracture toughness properties, as described in detail in U.S. Publi. 2003/0153984 which is incorporated by reference herein. This doped silicon nitride ceramic material has a relatively high flexural strength greater than about 700 Mega-Pascal (MPa) (e.g., between about 700 MPa and 1000 MPa) and a relatively high fracture toughness greater than about 7 Mega-Pascal root meter ($MPam^{0.5}$) e.g., between about 7 $MPam^{0.5}$ and 10.5

MPam$^{0.5}$). This high strength and high toughness doped silicon nitride ceramic achieves ultra-low wear over an extended service life, with dramatically reduced risk of brittle fracture. Powders of silicon nitride (Si$_3$N$_4$) and dopants such as alumina (Al$_2$O$_3$), yttria (Y$_2$O$_3$), magnesium oxide, and strontium oxide were conventionally processed to form a doped composition of silicon nitride. The dopant amount was optimized to achieve the highest density and mechanical properties. The homogeneous powders were then cold isostatic pressed at 300 Mega-Pascal (MPa) followed by sintering in a controlled atmosphere. Some cold isostatically pressed bars were hot isostatically pressed. A sintering temperature of 1875 degrees Celcius was found optimal to achieve high density, absence of pores and other flaws and a uniform fine-grained microstructure. The best combination of density and mechanical properties was achieved with Si$_3$N$_4$ doped with 6 weight % Y$_2$O$_3$+4 weight % Al$_2$O$_3$. In another preferred embodiment, the biocompatible ceramic has a flexural strength greater than about 800 Mega-Pascal (MPa) and a toughness greater than about 9 Mega-Pascal root meter (Mpam$^{0.5}$). Flexural strength was measured on standard 3-point bend specimens per American Society for Testing of Metals (ASTM) protocol method C-1161 and fracture toughness measured using single edge notched beam specimens per ASTM protocol method E399.

In the preferred form as shown best in FIG. 3, this high strength and high toughness ceramic material is used to form the substrate 30 of the ceramic acetabular cup 12. In this regard, the substrate 30 of the ceramic cup 12 has a relatively low porosity, and thus exhibits high density and high structural integrity generally consistent with and generally mimicking the characteristics of natural cortical bone lined with smooth lubricious articular cartilage. FIG. 3 further shows a surface coating or lining 14 formed on the part-spherical upwardly presented surface or convex upper side of the cup 12, wherein this coating or lining exhibits a comparatively greater or higher porosity that is generally consistent With and generally mimics the characteristics of natural cancellous bone. As a result, this higher porosity surface coating or lining 14 provides an effective bone ingrowth surface for achieving secure and stable bone ingrowth affixation of the ceramic acetabular cup 12 within the patient's acetabulum.

While persons skilled in the art will recognize and appreciate that the specific material used for the bone ingrowth surface coating or lining 14 may vary, a preferred porous material comprises a ceramic porous ingrowth surface material. In this regard, U.S. Pat. No. 6,846,327 which is incorporated by reference herein discloses a ceramic bone graft component having relatively high flexural strength and relatively high toughness properties yet defining first and second regions of comparatively lower and higher porosity to respectively mimic natural cortical and cancellous bone structures. These regions of different porosity may be unitarily constructed or otherwise integrated into a common or monolithic ceramic component having a variable porosity gradient. In a preferred form, the ceramic cup 12 has a porosity gradient ranging from about 2% to about 80% by volume, with the higher porosity region having a porosity in the range of from about 30% to about 80% by volume, and with overall pore sizes ranging from about 100 microns to about 500 microns. In use, the relatively low porosity region of the ceramic material provides a dense and hard structure with high structural strength and integrity, whereas the higher porosity or less dense region is suitable for bone ingrowth to achieve secure and stable implant affixation.

U.S. Pat. No. 6,846,327 discloses a preferred alumina-zirconia ceramic material having a zirconia composition of about 10% to about 20% by volume, with either yttria stabilized zirconia (about 2.5 to about 5 mol % yttria in zirconia) or ceria stabilized zirconia (about 2.5 to about 15 mol % ceria in zirconia) for the zirconia phase. The resultant ceramic material exhibits a highly desirable combination of high flexural strength (greater than about 500 MPa) and high fracture toughness (greater than about 5 MPam$^{0.5}$). Such alumina-zirconia based ceramic material may be employed in the present invention for the ceramic acetabular cup 12, although the harder and tougher silicon nitride (S$_3$N$_4$) ceramic as described in U.S. Publi. 2003/0153984 is preferred.

FIG. 3 shows the ceramic acetabular cup 12 to include the substrate 30 formed from relatively low porosity ceramic material having the desired high strength and high toughness properties, such as the doped silicon nitride (S$_3$N$_4$) material described in the above-referenced U.S. Publi. 2003/1053984, wherein this low porosity ceramic material lines and defines the concave part-spherical cavity 28. FIG. 3 further shows the comparatively higher porosity bone ingrowth surface 14, formed preferably from a higher porosity ceramic material as described in the above-referenced U.S. Pat. No. 6,846,327, extending over a substantial area of the convex upper side of the acetabular cup 12. As noted, this bone ingrowth surface 14 may be formed integrally with or otherwise applied to the substrate 30.

The femoral head 16 is sized and shaped for articulatory reception within the acetabular cup cavity 28. In a preferred form as viewed in FIG. 2, the femoral head 16 is constructed from a ceramic material that is compatible with the ceramic cup material. In this regard, a preferred material for the femoral head 16 comprises a matching or identical high strength and high toughness ceramic material corresponding with the acetabular cup material, as disclosed in U.S. Publi. 2003/1053984. Alternately, as viewed in one preferred alternative unipolar embodiment of the invention depicted in FIG. 4, a modified femoral head 16' may be constructed from a biocompatible metal material, preferably such as a cobalt chrome alloy as disclosed in the above-referenced 2003/1053984.

Figure 5:
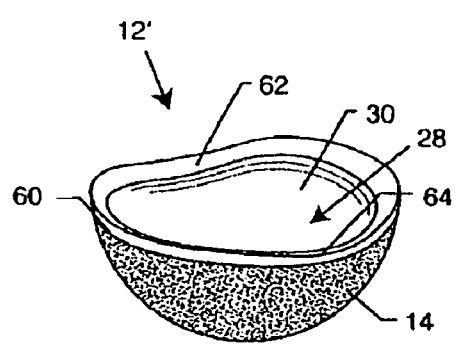
FIG. 5 is a perspective view illustrating an alternative preferred geometry for an acetabular cup component for use in the invention.
Figure 6:
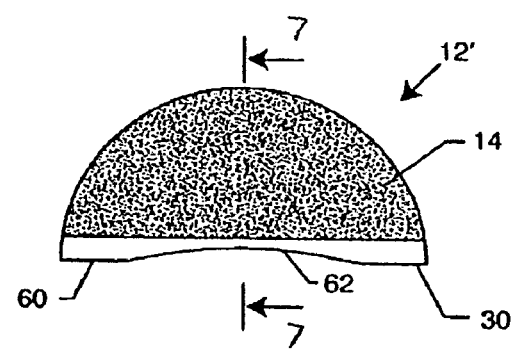
FIG. 6 is a side elevation view of the acetabular cup of FIG. 5.
Figure 7:
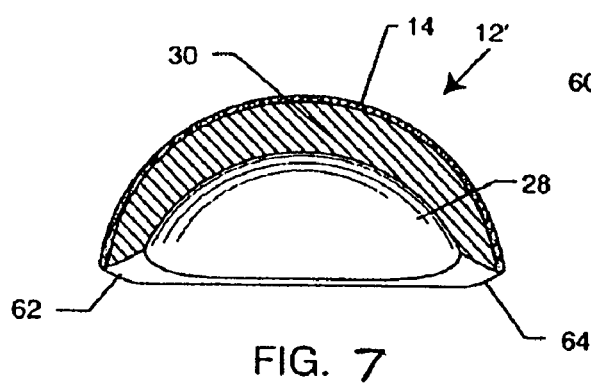
FIG. 7 is a sectional view taken generally on the line 7-7 of FIG. 6.

FIGS. 5-7 depict a modified ceramic acetabular cup 12' which may be incorporated into any one of the foregoing embodiments of the invention as shown in FIGS. 2-4 and previously described herein. In this regard, FIGS. 5-7 show the modified acetabular cup 12' to include the relatively low porosity substrate 30 defining the downwardly presented part-spherical cavity 28, in combination with the bone ingrowth coating or surface 14 on the upwardly presented or convex side thereof. Persons skilled in the art will appreciate that the bone ingrowth coating or surface may be omitted, as previously described herein. Importantly, the circumferential free edge or margin 60 of the ceramic cup 12' incorporates a pair of smoothly contoured, shallow relief segments 62 and 64 formed generally at diametrically opposed positions corresponding with the flexion/extension plane during normal patient movements. The inclusion of these shallow relief segments 62 and 64 beneficially provides the hip prosthesis and thus the patient with an enhanced range-of-motion (ROM).

A variety of further modifications and improvements in and to the hip prosthesis of the present invention will be apparent to persons skilled in the art. For example, it will be understood that the ceramic acetabular cup component as shown and described herein may be used for articulatory engagement with the natural ball-shaped femoral head at the upper end of the patient's femur, or with an appropriately capped natural femoral head, in lieu of a prosthetic femoral head. Accordingly, no limitation on the invention is intended by way of the foregoing description and accompanying drawings, except as set forth in the appended claims.

What is claimed is:

1. A hip joint prosthesis, comprising:
a monolithic acetabular cup defining a convex upper side having a size and shape adapted for seated engagement within a patient's natural acetabulum, and a lower side defining a downwardly open and generally part-spherical cavity lined by an articulation surface having a size and shape for articulatory reception of a matingly shaped femoral component;

said acetabular cup defining a relatively low porosity first region defining said articulation surface, and a comparatively higher porosity second region defining a bone ingrowth surface on said convex upper side thereof, wherein both of said first region and said second region comprise doped silicon nitride ceramic;

said doped silicon nitride ceramic of said relatively low porosity first region having a flexural strength greater than about 700 Mega-Pascal (MPa) and a fracture toughness greater than about 7 Mega-Pascal root meter (MPam$^{0.5}$), and comprising one or more dopants selected from the group of dopants consisting of yttrium oxide, magnesium oxide, strontium oxide, and alumina.

2. The hip joint prosthesis of claim 1 wherein said ceramic of said comparatively higher porosity second region has pores formed therein with a pore size ranging from about 100 microns to about 500 microns.

3. The hip joint prosthesis of claim 1 further comprising said matingly shaped femoral component wherein said matingly shaped femoral component comprises a ball-shaped femoral head.

4. The hip joint prosthesis of claim 3 wherein said femoral head is formed from a ceramic material.

5. The hip joint prosthesis of claim 3 wherein said femoral head is formed from a ceramic material substantially identical to the acetabular cup ceramic material.

6. The hip joint prosthesis of claim 3 wherein said femoral head is formed from a biocompatible metal.

7. A hip joint prosthesis, comprising:
a monolithic acetabular cup defining a convex upper side and having a size and shape adapted for seated engagement within a patient's natural acetabulum, and a lower side defining a downwardly open and generally part-spherical cavity lined by an articulation surface having a size and shape for articulatory reception of a matingly shaped femoral component;

said acetabular cup being formed from a doped silicon nitride ceramic material having a flexural strength greater than about 700 Mega-Pascal (MPa) and a fracture toughness greater than about 7 Mega-Pascal root meter (MPam$^{0.5}$), and comprising one or more dopants selected from the group of dopants consisting of yttrium oxide, magnesium oxide, strontium oxide, and alumina; and said acetabular cup having a rim defined by the circumferential free edge between said upper and lower sides, and wherein said rim includes a pair of generally identically-shaped and diametrically opposed recesses formed therein for increased range of motion, wherein each recess extends from said upper side to said lower side.

8. The hip joint prosthesis of claim 7 wherein said pair of generally identically-shaped and diametrically opposed recesses formed in said rim provides increased range of motion in a flexion/extension plane.

9. The hip joint prosthesis of claim 7 wherein said ceramic material has a flexural strength greater than about 800 Mega-Pascal (MPa) and a fracture toughness greater than about 9 Mega-Pascal root meter (MPam$^{0.5}$).

10. The hip joint prosthesis of claim 1 wherein said relatively high porosity second region has greater than 50% porosity to about 80% porosity.

11. The hip joint prosthesis of claim 1 wherein said ceramic of said relatively low porosity first region has a flexural strength greater than about 800 Mega-Pascal (MPa) and a fracture toughness greater than about 9 Mega-Pascal root meter (MPam$^{0.5}$).

12. The hip joint prosthesis of claim 1 wherein said ceramic of said relatively low porosity first region has a flexural strength of between about 700 MPa and 1000 MPa and a fracture toughness of between about 7 MPam$^{0.5}$ and 10.5 MPam$^{0.5}$.

13. The hip joint prosthesis of claim 7 wherein said ceramic material has a flexural strength of between about 700 MPa and 1000 MPa and a fracture toughness of between about 7 MPam$^{0.5}$ and 10.5 MPam$^{0.5}$.

* * * * *